US011344256B2

(12) United States Patent
Kirszenblat et al.

(10) Patent No.: US 11,344,256 B2
(45) Date of Patent: May 31, 2022

(54) COLLECTING BIOLOGICALLY-RELEVANT INFORMATION USING AN EARPIECE

(71) Applicant: BOSE CORPORATION, Framingham, MA (US)

(72) Inventors: Romain Kirszenblat, Allston, MA (US); Lifun Lin, Lincoln, MA (US); Mikhail Ioffe, Newton, MA (US)

(73) Assignee: BOSE CORPORATION, Framingham, MA (US)

( * ) Notice: Subject to any disclaimer, the term of this patent is extended or adjusted under 35 U.S.C. 154(b) by 75 days.

(21) Appl. No.: 16/549,792

(22) Filed: Aug. 23, 2019

(65) Prior Publication Data

US 2019/0380648 A1 Dec. 19, 2019

Related U.S. Application Data

(62) Division of application No. 15/438,213, filed on Feb. 21, 2017, now abandoned.

(51) Int. Cl.
*A61B 5/00* (2006.01)
*A61B 5/021* (2006.01)
(Continued)

(52) U.S. Cl.
CPC ............ *A61B 5/6803* (2013.01); *A61B 5/021* (2013.01); *A61B 5/02125* (2013.01); *A61B 5/1102* (2013.01); *A61B 5/14517* (2013.01); *A61B 5/14539* (2013.01); *A61B 5/25* (2021.01); *A61B 5/296* (2021.01); *A61B 5/398* (2021.01);
(Continued)

(58) Field of Classification Search
CPC .......................... A61B 5/0408; A61B 5/04085
See application file for complete search history.

(56) References Cited

U.S. PATENT DOCUMENTS

| 5,712,917 A | 1/1998 | Offutt |
| 6,353,396 B1 | 3/2002 | Atlas |

(Continued)

FOREIGN PATENT DOCUMENTS

| CN | 102596021 A | 7/2012 |
| CN | 104323764 A | 2/2015 |

(Continued)

OTHER PUBLICATIONS

Google/Machine translation of CN-106994014-A (Year: 2017).*

(Continued)

*Primary Examiner* — Shirley X Jian
(74) *Attorney, Agent, or Firm* — Patterson + Sheridan, LLP

(57) ABSTRACT

Aspects of the present disclosure provide a method for obtaining biological information associated with a user, comprising receiving electrical signals via a first electrode on an ear tip of an earpiece inserted in an ear of the user, receiving electrical signals via a second electrode on an external portion of the earpiece, and deriving an electrocardiogram (ECG) based on the signals received via the first electrode and the second electrode. Aspects also provide a method for determining a pulse travel time (PTT) associated with a user, comprising obtaining a proximal signal using an earpiece inserted in of the user, obtaining a distal signal using the earpiece, and deriving the PTT based on the obtained proximal signal and the obtained distal signal.

12 Claims, 16 Drawing Sheets

(51) Int. Cl.
  *A61B 5/11* (2006.01)
  *A61B 5/145* (2006.01)
  *A61B 7/04* (2006.01)
  *A61B 5/25* (2021.01)
  *A61B 5/296* (2021.01)
  *A61B 5/398* (2021.01)
  *A61B 5/0533* (2021.01)
  *A61B 5/024* (2006.01)
  *A61B 5/291* (2021.01)

(52) U.S. Cl.
  CPC .............. *A61B 5/6817* (2013.01); *A61B 7/04* (2013.01); *A61B 5/02416* (2013.01); *A61B 5/0533* (2013.01); *A61B 5/291* (2021.01); *A61B 2562/0209* (2013.01); *A61B 2562/0219* (2013.01)

(56) References Cited

U.S. PATENT DOCUMENTS

| | | | |
|---|---|---|---|
| 8,706,206 | B2 | 4/2014 | Kanai et al. |
| 9,474,876 | B1 | 10/2016 | Kahn et al. |
| 9,516,442 | B1 | 12/2016 | Dusan et al. |
| 9,522,317 | B2 | 12/2016 | Bleich et al. |
| 9,707,466 | B2 | 7/2017 | Bleich et al. |
| 9,867,571 | B2* | 1/2018 | Aimone .................. A61B 5/291 |
| 9,872,628 | B2* | 1/2018 | Hyde .................. A61B 5/6806 |
| 9,918,650 | B2* | 3/2018 | Kilsgaard .............. A61B 5/291 |
| 9,956,470 | B2 | 5/2018 | Bleich et al. |
| 10,213,157 | B2 | 2/2019 | Farrell et al. |
| 10,575,777 | B2* | 3/2020 | Ayers .................. H04R 1/1016 |
| 10,835,145 | B1* | 11/2020 | Prevoir ................ H04R 1/1016 |
| 11,103,692 | B2* | 8/2021 | Cakmak .............. A61B 5/6817 |
| 11,241,574 | B2* | 2/2022 | Trotter .............. A61N 1/36082 |
| 2004/0073129 | A1 | 4/2004 | Caldwell et al. |
| 2004/0252103 | A1 | 12/2004 | Bonnat |
| 2005/0192514 | A1 | 9/2005 | Kearby et al. |
| 2006/0013079 | A1* | 1/2006 | Rekimoto ................ G06F 3/165 369/30.01 |
| 2007/0066914 | A1 | 3/2007 | Le et al. |
| 2007/0112277 | A1 | 5/2007 | Fischer et al. |
| 2007/0250145 | A1* | 10/2007 | Kraus ................ A61N 1/36017 607/136 |
| 2008/0146892 | A1 | 6/2008 | LeBoeuf et al. |
| 2008/0187147 | A1 | 8/2008 | Berner et al. |
| 2008/0306398 | A1 | 12/2008 | Uchiyama et al. |
| 2010/0217100 | A1 | 8/2010 | LeBoeuf et al. |
| 2011/0040202 | A1 | 2/2011 | Luo et al. |
| 2011/0071416 | A1 | 3/2011 | Terada et al. |
| 2011/0190600 | A1 | 8/2011 | McKenna et al. |
| 2012/0128166 | A1 | 5/2012 | Kim et al. |
| 2012/0165695 | A1 | 6/2012 | Kidmose et al. |
| 2012/0177233 | A1* | 7/2012 | Kidmose ................ A61B 5/121 381/314 |
| 2012/0203077 | A1* | 8/2012 | He ..................... A61B 5/02125 600/301 |
| 2012/0203079 | A1 | 8/2012 | McLaughlin |
| 2012/0209101 | A1* | 8/2012 | Kidmose .............. B29C 64/386 600/379 |
| 2012/0226127 | A1 | 9/2012 | Asjes et al. |
| 2012/0238856 | A1 | 9/2012 | Kidmose et al. |
| 2012/0289869 | A1 | 11/2012 | Tyler |
| 2013/0056010 | A1 | 3/2013 | Walker et al. |
| 2013/0131537 | A1 | 5/2013 | Tam |
| 2013/0234823 | A1 | 9/2013 | Kahn et al. |
| 2013/0242262 | A1 | 9/2013 | Lewis |
| 2013/0296731 | A1* | 11/2013 | Kidmose .............. A61B 5/6817 600/544 |
| 2013/0317382 | A1 | 11/2013 | Le |
| 2013/0338738 | A1 | 12/2013 | Garcia Molina et al. |
| 2013/0343585 | A1 | 12/2013 | Bennett et al. |
| 2014/0051940 | A1 | 2/2014 | Messerschmidt |
| 2014/0135644 | A1 | 5/2014 | Kim |
| 2014/0136450 | A1 | 5/2014 | Lee |
| 2014/0148657 | A1 | 5/2014 | Hendler et al. |
| 2014/0148724 | A1* | 5/2014 | Ungstrup ............... H04R 25/70 600/544 |
| 2014/0148872 | A1 | 5/2014 | Goldwasser et al. |
| 2014/0160250 | A1 | 6/2014 | Pomerantz et al. |
| 2014/0160424 | A1 | 6/2014 | Benko et al. |
| 2014/0171775 | A1* | 6/2014 | Kilsgaard ............ A61B 5/6817 600/379 |
| 2014/0171820 | A1 | 6/2014 | Causevic |
| 2014/0180158 | A1 | 6/2014 | Cheng et al. |
| 2014/0194702 | A1 | 7/2014 | Tran |
| 2014/0206323 | A1 | 7/2014 | Scorcioni |
| 2014/0211593 | A1 | 7/2014 | Tyler et al. |
| 2014/0213874 | A1 | 7/2014 | Tong et al. |
| 2014/0221779 | A1 | 8/2014 | Schoonover et al. |
| 2014/0223462 | A1 | 8/2014 | Aimone et al. |
| 2014/0267005 | A1 | 9/2014 | Urbach |
| 2014/0267401 | A1 | 9/2014 | Urbach |
| 2014/0275875 | A1 | 9/2014 | Su et al. |
| 2014/0276183 | A1 | 9/2014 | Badower |
| 2014/0277582 | A1 | 9/2014 | Leuthardt et al. |
| 2014/0288614 | A1 | 9/2014 | Hagedorn et al. |
| 2014/0316230 | A1 | 10/2014 | Denison et al. |
| 2014/0323900 | A1 | 10/2014 | Bibian et al. |
| 2014/0333529 | A1 | 11/2014 | Kim et al. |
| 2014/0337036 | A1 | 11/2014 | Haiut et al. |
| 2014/0375545 | A1 | 12/2014 | Ackerman et al. |
| 2015/0005841 | A1 | 1/2015 | Pal et al. |
| 2015/0018705 | A1 | 1/2015 | Barlow et al. |
| 2015/0079560 | A1 | 3/2015 | Cowan |
| 2015/0080746 | A1 | 3/2015 | Bleich et al. |
| 2015/0297109 | A1 | 10/2015 | Garten et al. |
| 2016/0081572 | A1 | 3/2016 | Hong et al. |
| 2016/0239937 | A1 | 8/2016 | Kim et al. |
| 2016/0241947 | A1 | 8/2016 | Degraye et al. |
| 2016/0330182 | A1 | 11/2016 | Jeon et al. |
| 2016/0353195 | A1 | 12/2016 | Lott |
| 2016/0367189 | A1* | 12/2016 | Aimone .................. A61B 5/291 |
| 2017/0000370 | A1* | 1/2017 | Hyde .................. A61B 5/0245 |
| 2017/0071525 | A1 | 3/2017 | Lin et al. |
| 2017/0095721 | A1 | 4/2017 | Bleich et al. |
| 2017/0100032 | A1 | 4/2017 | Zakariaie et al. |
| 2017/0142507 | A1 | 5/2017 | Chang et al. |
| 2017/0173296 | A1 | 6/2017 | Park et al. |
| 2017/0195794 | A1 | 7/2017 | Vaynberg et al. |
| 2017/0312612 | A1 | 11/2017 | Bleich et al. |
| 2018/0014741 | A1 | 1/2018 | Chou |
| 2018/0020937 | A1 | 1/2018 | Chou |
| 2018/0235540 | A1 | 8/2018 | Kirszenblat et al. |
| 2018/0333056 | A1 | 11/2018 | Chou |
| 2019/0053756 | A1* | 2/2019 | Ayers ..................... G06F 3/017 |
| 2019/0151646 | A1* | 5/2019 | Cakmak .............. A61N 1/36036 |
| 2019/0223747 | A1* | 7/2019 | Chou .................. A61B 5/681 |
| 2019/0380597 | A1* | 12/2019 | Howard .............. H04R 1/1016 |
| 2021/0069488 | A1* | 3/2021 | Trotter .............. A61N 1/36078 |
| 2021/0077812 | A1* | 3/2021 | Hool .................. A61N 1/37211 |
| 2022/0015703 | A1* | 1/2022 | Mirov ................. A61B 5/291 |

FOREIGN PATENT DOCUMENTS

| | | | |
|---|---|---|---|
| CN | 105284125 A | | 1/2016 |
| CN | 106994014 A | * | 8/2017 |
| WO | 2005020841 A2 | | 3/2005 |
| WO | 2014205327 A1 | | 12/2014 |
| WO | 2016083807 A1 | | 6/2016 |
| WO | 2016119664 A1 | | 8/2016 |

OTHER PUBLICATIONS

Tronstad, et al. "Electrical Measurement of Sweat Activity", Physiological Measurement, vol. 29, No. 6, Jun. 1, 2008, pp. S409-S415.
International Search Report and Written Opinion for International Application No. PCT/US2018/034401, dated Sep. 3, 2018, 12 pp.
Kidmose, et al., "A Study of Evoked Potentials From Ear-EEG", IEEE Transactions on Biomedical Engineering, vol. 60, No. 10, Oct. 2013.

(56) References Cited

OTHER PUBLICATIONS

Goverdovsky, et al., "Hearables: Multimodal Physiological In-Ear Sensing", Scientific Reports, www.nature.com/scientificreports, published online Jul. 31, 2017.
Kappel, et al., "Study of Impedance Spectra for Dry and Wet EarEEG Electrodes", 2015 37th Annual International Conference of the IEEE Engineering in Medicine and Biological Society, Aug. 2015.
Kappel, et al., "Dry-Contact Electrode Ear-EEG" IEEE Transactions on Biomedical Engineering, 2018.
Looney, et al., "The In-the-Ear Recording Concept", IEEE Pulse, Nov./Dec. 2012.
International Search Report and Written Opinion for International Application No. PCT/US2018/014887, dated Mar. 21, 2018, 12 pp.
First Office Action for Chinese Application No. 201880021748.6 dated Sep. 1, 2021.
Patent Search Report for Chinese Application No. 201880021748.6 dated Aug. 18, 2021.

* cited by examiner

COLLECTING BIOLOGICALLY-RELEVANT INFORMATION USING AN EARPIECE

CROSS-REFERENCE TO RELATED APPLICATIONS

This application is a divisional application of co-pending U.S. patent application Ser. No. 15/438,213, titled "COLLECTING BIOLOGICALLY-RELEVANT INFORMATION USING AN EARPIECE," filed Feb. 21, 2017. The aforementioned patent application is herein incorporated by reference in its entirety.

BACKGROUND

Aspects of the present disclosure generally relate to using an earpiece configured to collect biologically-relevant information and methods for collecting biologically-relevant information using, at least, information collected via a surface of the ear canal or the outer ear.

Monitoring biologically-relevant information helps to determine a variety of characteristics of an individual. As an example, physiological sensing, biochemical sensing, and motion sensing, either alone or in combination, are used to monitor an individual's health. Monitoring the individual's health helps in preventative care and with the diagnosis and treatment of diseases.

As a growing segment of the population ages and as the number of individuals with chronic conditions increases, it is desirable to continuously improve the methods by which health-related parameters are collected and processed. Several challenges exist in improving the method and apparatuses used for collecting information using for health-monitoring. The method and apparatus for obtaining the information should be convenient, comfortable for the user, and accurate. Furthermore, health related parameters should be collected in a continuous and nonintrusive manner.

SUMMARY

Certain aspects provide a method for obtaining biological information associated with a user. The method includes receiving electrical signals via a first electrode on an ear tip of an earpiece inserted in an ear of the user, receiving electrical signals via a second electrode on an external portion of the earpiece, and deriving an electrocardiogram (ECG) based on the electrical signals received via the first electrode and the second electrode.

According to aspects, the method further comprises determining a difference in potential between the electrical signals received via the first electrode and the electrical signals received via the second electrode. The ECG is derived based on the determined difference in potential. According to aspects, the method further comprises determining a blood pressure associated with the user based on the derived ECG.

According to aspects, the electrical signals received via the first electrode are obtained from the ear of the user, and the electrical signals received via the second electrode are obtained from another location of the user having a different potential than the ear. According to one example, the method includes contacting a finger of the left hand of the user on the second electrode to obtain the electrical signals via the second electrode.

As described herein, the ear tip comprises a flexible, umbrella shaped ear tip.

Certain aspects provide a method for determining a pulse travel time (PTT) associated with a user. The method includes obtaining a proximal signal using an earpiece inserted in an ear of the user, obtaining a distal signal using the earpiece, and deriving the PTT based on the obtained proximal signal and the obtained distal signal.

According to aspects, the proximal signal comprises an electrocardiogram (ECG) pulse signal, and the distal signal comprises one of a phonocardiogram (PCG) signal obtained via a microphone located on the earpiece or a photoplethysmogram (PPG) signal obtained via an optical sensor on the earpiece.

According to aspects, the proximal signal comprises an electrocardiogram (ECG) pulse signal, and the distal signal comprises a ballistocardiogram (BCG) signal obtained via an accelerometer on the earpiece.

According to aspects, the proximal signal comprises a ballistocardiogram (BCG) signal obtained via an accelerometer on the earpiece, and the distal signal comprises one of a phonocardiogram (PCG) signal obtained via a microphone located on the earpiece or a photoplethysmogram (PPG) signal obtained via an optical sensor on the earpiece.

According to aspects, deriving the PTT comprises computing a delay between the proximal and distal signals. According to one example, the method further comprises determining a blood pressure of the user based on the computed delay.

Certain aspects provide an earpiece comprising a flexible, conductive ear tip, configured to receive electrical signals from a user of the earpiece and a housing coupled with the conductive ear tip, wherein the housing is configured to transfer the electrical signals from the conductive tip to external electronic hardware.

According to aspects, the conductive ear tip comprises at least one of an ear tip coated with conductive coating or an ear tip fabricated with conductive rubber. According to aspects, the conductive ear tip comprises two or more sections, each section having its own electrical contact for collecting electrical signals from the user.

According to aspects, a biosensor placed on the earpiece, wherein the biosensor is configured to monitor at least one of sweat composition of pH associated with the user.

According to aspects, the conductive ear tip is configured to transfer signals from the biosensor to the housing.

According to aspects, the earpiece comprises a multi-conductive electrode for monitoring Galvanic Skin Response (GSR) of the user.

According to aspects, the electrical signals collected by the conductive tip are used to produce at least one of an electroencephalogram (EEG), electrocardiogram (ECG), electromyogram (EMG), or electrooculogram (EOG), associated with the user.

According to aspects, the conductive ear tip comprises an umbrella shaped ear tip and is configured to create a seal with an ear canal of the user.

According to aspects, the earpiece comprises a shaft region between the umbrella shaped tip and the housing, and an electrical wire for transmitting the electrical signals from the shaft region to the housing, the electrical wire having a first end and a second end, wherein the first end is coupled with the shaft region and the second end is coupled with the housing.

According to aspects, the conductive ear tip comprises a first electrode and a second electrode, the first electrode extending into an ear canal of the user and the second electrode located on a surface of the tip external to the ear canal when the tip is positioned in the ear canal, wherein the first electrode and second electrode comprise a sensor for collecting biologically relevant information associated with the user. According to an example, the first electrode is coated with a silver-based conductive coating and comprises a negative electrode and the second electrode comprises an isolated conductive coated section of one of the tip or the housing. According to one example, the second electrode comprises a portion of the housing covered with copper foil.

According to aspects, the earpiece further comprises at least one of a microphone, accelerometer, or optical sensor configured to collect biologically relevant information associated with the user.

DETAILED DESCRIPTION

Aspects of the present disclosure relate to using an earpiece as a wearable health monitoring system. Accordingly, biologically-relevant information is collected via the earpiece inserted in an ear of a user. According to one example, an earpiece is used to measure at least one of the blood pressure, respiration rate, heart rate, or heart rate variability of a user continuously and non-intrusively. As described herein, the earpiece is used to collect one or more of a pulse travel time (PTT), an electroencephalogram (EEG), electrocardiogram (ECG), electromyogram (EMG), electrooculogram (EOG), galvanic skin response (GSR), sweat composition, or pH associated with the user of the earpiece.

Several factors contribute to a desirable, continuous, wearable health monitoring system. A practical wearable system should not be clearly stigmatizing. Preferably, the health monitoring system is unobtrusive and discrete so as to provide some privacy. The system should be comfortable to wear with minimum interference to the user's activities. A comfortable and non-intrusive system ensures that the recordings are carried out when users are monitored in their natural environment, and therefore enables the acquisition of more representative, useful, and realistic data. The system should be embedded onto a device that ensures the electrodes and sensors are firmly held in position. Accordingly, the electrodes or sensors are not easily damaged or dislodged from the system. The system should be user friendly. For example, users should be able to use the system absent assistance from a trained professional. In this manner, the health monitoring system reduces operational costs. Finally, a desirable system is realistic, evidenced by feasibility of manufacturing.

The in-ear health monitoring system described herein advantageously fulfills the factors described above. In-ear headphones, which include one or two earpieces with removable and replaceable soft ear tips, are commercially available and widely-used for both communication and entertainment purposes. As will be described in more detail below, an ear tip may include a soft, flexible tip and a tail. Soft, flexible tips enhance the acoustic experience of a user by providing acoustic sealing with the ear and mechanical stability. The tips are umbrella shaped and made of a flexible material to comfortably seal with the ear. Aspects of the present disclosure provide at least one electrode on an ear tip of an earpiece used to receive electrical signals from a user. The electrical signals are used to collect biologically-relevant information.

Figure 1:
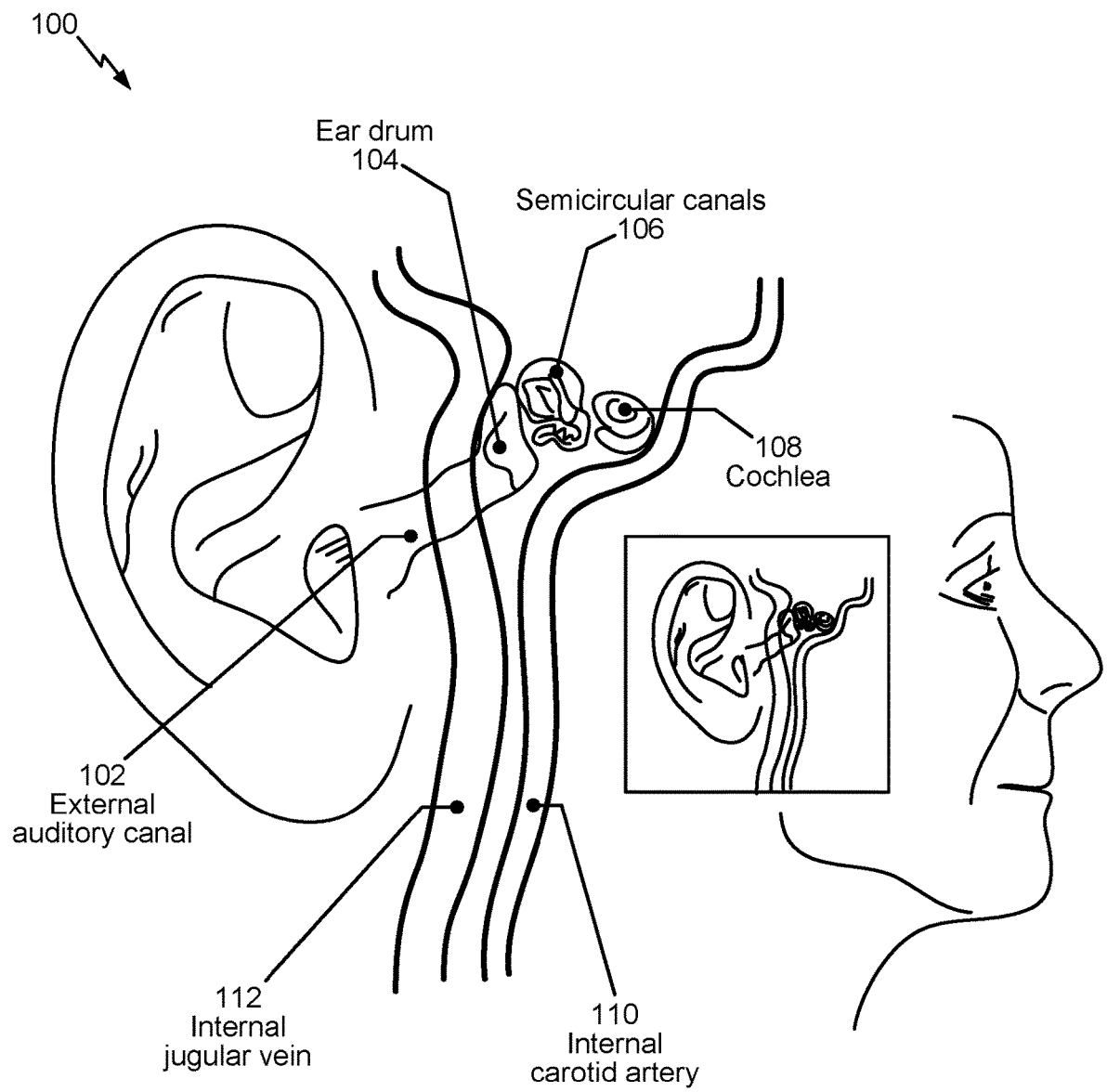
FIG. 1 illustrates the anatomy of a human ear.

FIG. 1 illustrates the anatomy 100 of a human ear. The external auditory canal, or ear canal, 102 is a passageway that leads from the outside of the head to the ear drum 104. The ear drum 104, which separates the external ear from the middle ear, transmits sound from the air to the middle ear. The sound then travels to the semicircular canals 106 and cochlea 108 in the inner ear. The internal carotid artery 110 is a major artery supplying the brain. The internal jugular vein 112 drains blood from the head, brain, face, and neck and conveys it toward the heart.

As will be described with reference to the figures, the earpiece used for collecting biologically-relevant information advantageously includes a flexible, ear tip which creates a gentle seal with the ear canal 102. The flexible ear tip has an umbrella shape which allows a mass-producible earpiece capable of conforming to the interior shape and form of a wide range of individual ear canals. The ear tip also includes a tail portion, extending from the umbrella shaped tip. Examples of such ear tips used to collect biological information for health monitoring are illustrated in FIGS. 3, 4, 6, and 8-14.

Example Use of a Conductive Earpiece

The following paragraphs describe an example of using earpieces with electrodes. According to one example, a conductive ear tip is used to determine an ECG of a user.

Figure 2:
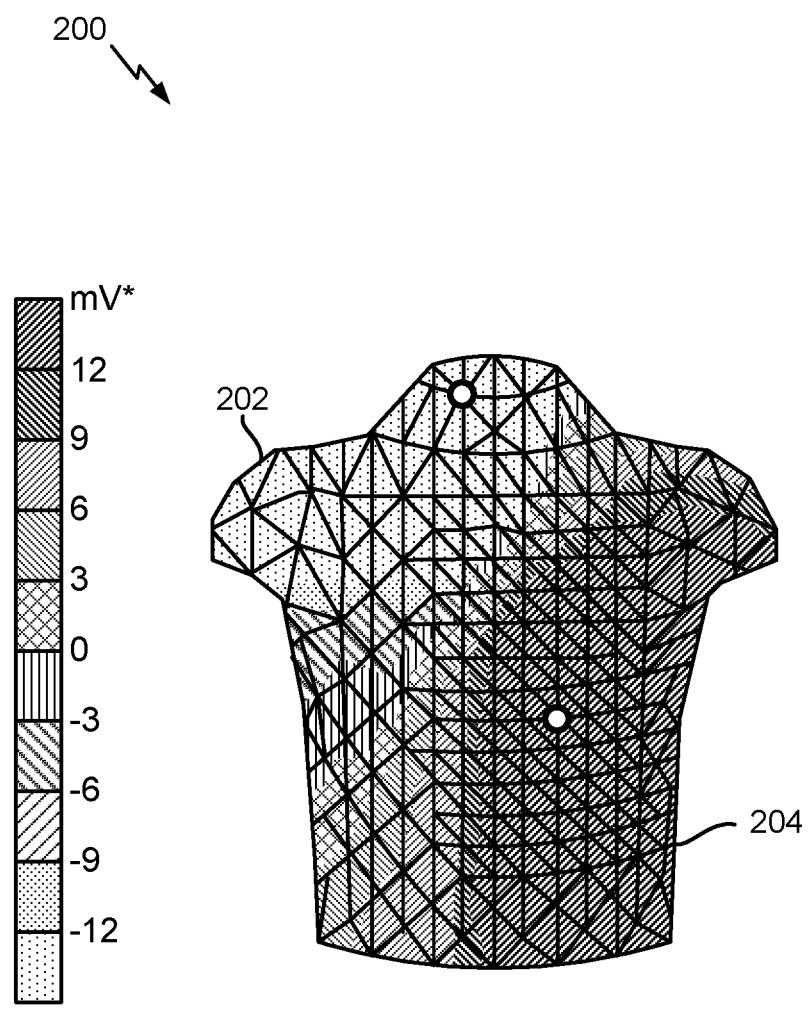
FIG. 2 illustrates an example body surface potential map.

FIG. 2 illustrates an example body surface potential map 200. The potential values illustrated in FIG. 2 are provided for illustrative purposes only. More generally, potentials on the body vary from highly positive 204 to highly negative 202.

An ECG signal can be measured using two locations on the body with similar potentials. Accordingly, an ECG signal can be measured based on signals received from a left and right ear. However, it is desirable to measure an ECG signal using two anatomical locations having potentials different enough to allow obtaining a good signal to noise ratio.

According to one example, a finger on the left hand has a highly positive potential, while both ears have highly negative potentials. A finger on the right hand or any other anatomical area can be used to measure an ECG signal in combination with the ear, but the left hand will provide a better signal to noise ratio.

Figure 3:
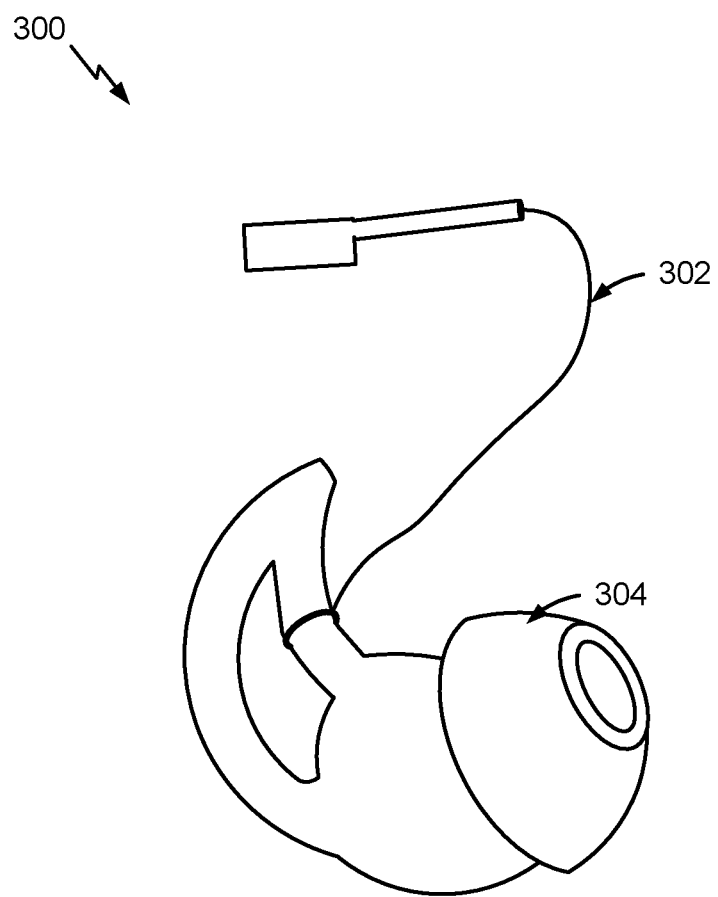
FIG. 3 illustrates an example earpiece having a flexible, coated ear tip.

FIG. 3 illustrates an example earpiece 300 having a flexible, coated ear tip 304. The ear tip provides enough surface area contact with the skin to provide a usable signal for determining an ECG. The soft, flexible material of the tip helps the tip to conform to the ear geometry and increases the surface area having contact with a user's skin. Additionally, the flare of the umbrella shaped tip provides some springiness so that some pressure is exerted by the tip on the skin. This pressure helps to lower the contact resistance between the coating of the ear tip and the ear tip itself.

A first, negative, electrode is formed by the ear tip 304, coated with conductive material or fabricated with conductive material, inserted in the ear canal. According to one example, a wire 302 running through the earpiece conveys the signal to external, electronic hardware. According to another example, the signal is wirelessly conveyed to external electronic hardware.

Figure 4:
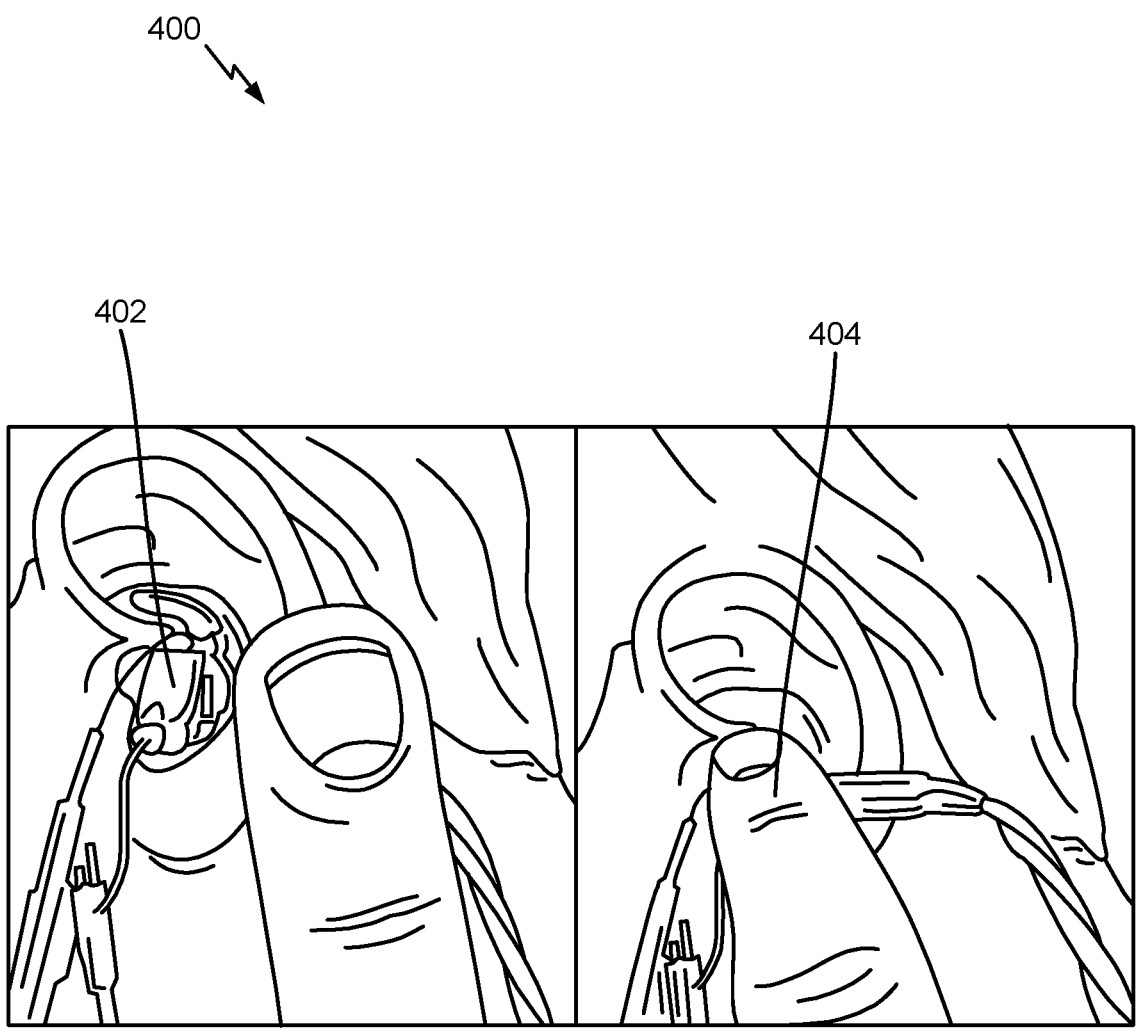
FIG. 4 illustrates an example of an electrode on an outside surface of the earpiece.

FIG. 4 illustrates an example 400 of an electrode on an outside surface of the earpiece. In one example, a second electrode may be any electrically isolated and conductive region on the ear tip, tail or the housing. An electrode on the outside surface of the earpiece is an electrically isolated conductive region formed by coating the ear tip or using conductive rubber to fabricate the ear tip. According to one example, the electrode on the outer part of the earpiece is covered with copper foil. The copper foil forms a second, positive electrode.

After the ear tip 402 is placed in the ear, at, 404, the user contacts the isolated conductive region with a finger of the left hand. According to this example, the combination of the first and second electrodes form the ECG sensor—the left hand and either ear being at potential of opposite signs. In other examples, the combination of the first and second electrodes may form an electrical sensor for determining an EEC, EMG, or EOG.

Figure 5:
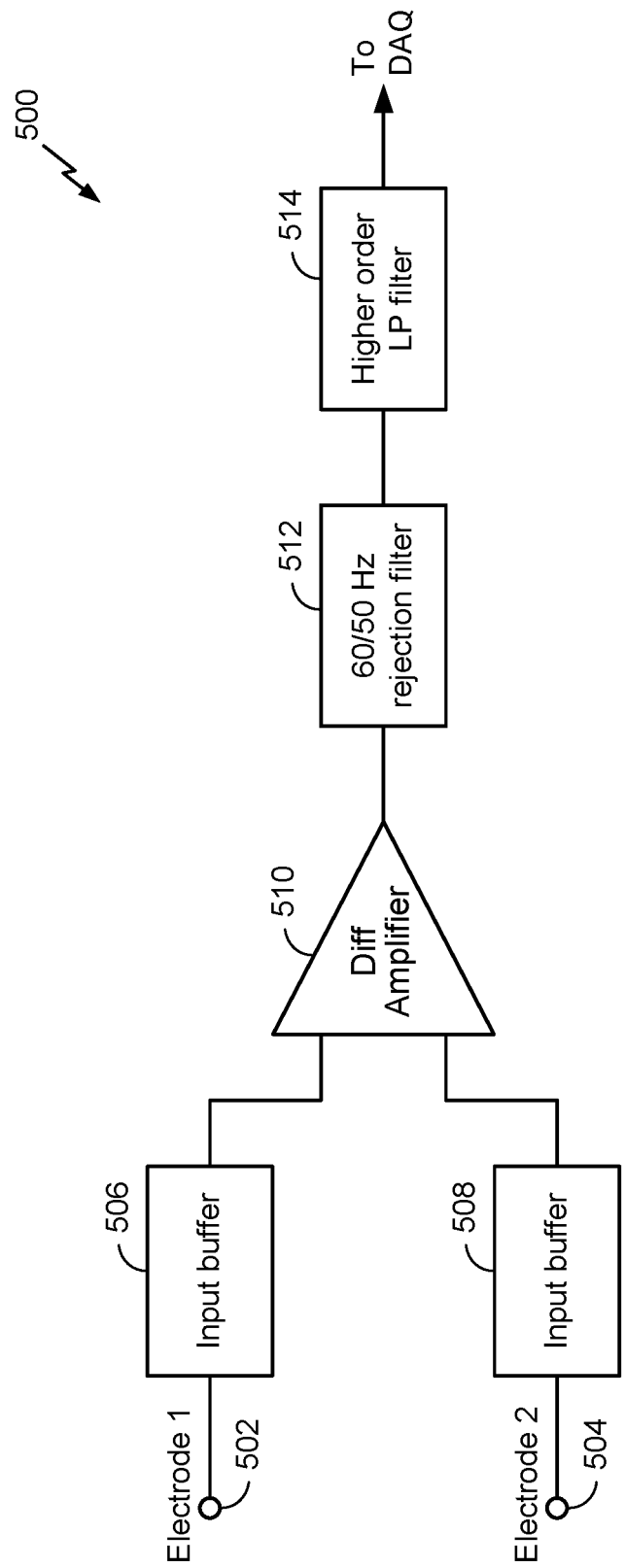
FIG. 5 illustrates an example of the electronic hardware coupled to the ear tip that processes the signals from the first and second electrodes of the earpiece.

FIG. 5 illustrates an example 500 of the electronic hardware coupled to the ear tip that processes the signals from the first and second electrodes of the earpiece.

The first electrode 502 and the second electrode 504 are coupled to input buffers 506 and 508, respectively.

The input buffers 506 and 508 are high impedance amplifiers. The input buffers match the high impedance of the electrodes 502 and 504 to the relatively low impedance of connecting cables or wires. The input buffers are placed as close as possible to the electrodes to minimize the length of high impedance connections, thereby minimizing effects of external electric field interference.

Signals from input buffers 506 and 508 are connected to inputs of a differential amplifier 510. The differential amplifier 510 amplifies the difference between the electrode signals and suppresses unwanted common mode interference signals.

50/60 Hz AC power lines can cause harmful, strong interference to ECG measurement. Accordingly, a rejection filter 512 tuned to the AC line main frequency removes the 50/60 Hz signal from the output of differential amplifier 1310.

A higher-order low pass filter 514 suppresses harmonics of 50/60 Hz AC power line interference before the electrical signal is fed to a data acquisition system. The arrangement of the filters 512 and 514 is needed for an efficient utilization of dynamic range and resolution of data acquisition system.

As a general matter, all the elements of FIG. 5 may be included in a single integrated circuit, or in discrete components.

Example Derivation of Pulse Travel Time

One technique for determining blood pressure uses the pulse travel time (PTT), generally the time it takes each pulse to travel from the heart to the point at which it is measured. PTT is derived using two signals between which a delay exists. One sensor is used to measure a proximal signal and another sensor is used to measure a distal signal. The delay between the proximal signal and the distal signal is inversely correlated to a user's blood pressure. The greater the delay between the two signals, the higher the blood pressure prediction accuracy.

The order of arrival of the signals at the sensor location is: (1) electrocardiogram (ECG) pulse signal, (2) ballistocardiogram (BCG) signal, and (3) photoplethysmogram (PPG) or in-ear phonocardiogram (PCG) pulse signal. ECG and BCG represent the heartbeat, and can be detected at the same site as the pulse, as the delay due to the speed of electric or acoustic waves through the body is much less than the delay of the pulse wave through the blood, which is detected by the PPG or PCG. The BCG signal may be obtained using an accelerometer placed on the ear tip. The PPG signal may be obtained using an optical sensor on the ear tip. The PCG signal may be obtained using a microphone on the ear tip. The accelerometer and microphone do not need to contact the skin; accordingly, they may be placed anywhere on the ear tip with sufficient acoustic coupling to the body to detect the signals.

According to one example, the ECG pulse signal is the proximal signal and a PPG or an in-ear phonocardiogram PCG pulse signal is the distal signal. Advantageously, this combination of proximal and distal signals provides a large delay. In particular, the delay between ECG and the pulse signal is, within sensing tolerances, equivalent to the PTT. According to another example, an accelerometer providing a ballistocardiogram (BCG) signal is used to compute a PTT. The BCG signal is the proximal signal and the PPG or PCG pulse signal is the distal signal. According to another example, the accelerometer signal is the distal signal and the ECG pulse signal is the proximal signal.

Figure 6:
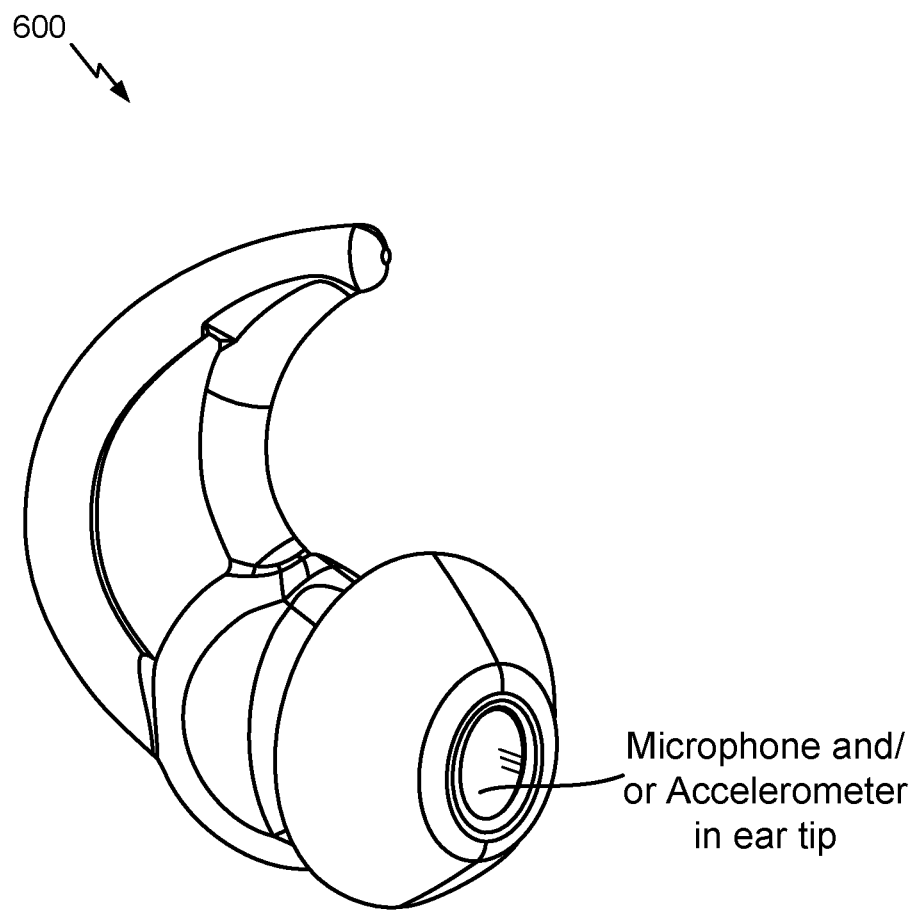
FIG. 6 illustrates a microphone or accelerometer placed in the ear tip of an earpiece.

FIG. 6 illustrates a microphone or accelerometer placed in the ear tip of an earpiece 600. According to an example, a microphone, such as a MicroElectrical-Mechanical System (MEMS) microphone, placed in the ear tip is used to obtain an in-ear PCG signal. As illustrated in FIG. 1, the internal carotid artery 110 runs close to the ear canal 102 and is likely to be the cause of a received acoustic signal. Additionally or alternatively, an accelerometer is placed in the ear tip. The microphone and accelerometer may be placed anywhere on the earpiece 600 that it is acoustically coupled to the user's body, because they do not need to contact the skin. For example, a microphone coupled to the air inside the ear canal can detect the sound of the pulse without directly contacting the body. According to an example, the accelerometer is attached to the housing and is therefore mechanically coupled to the user.

Figure 7:
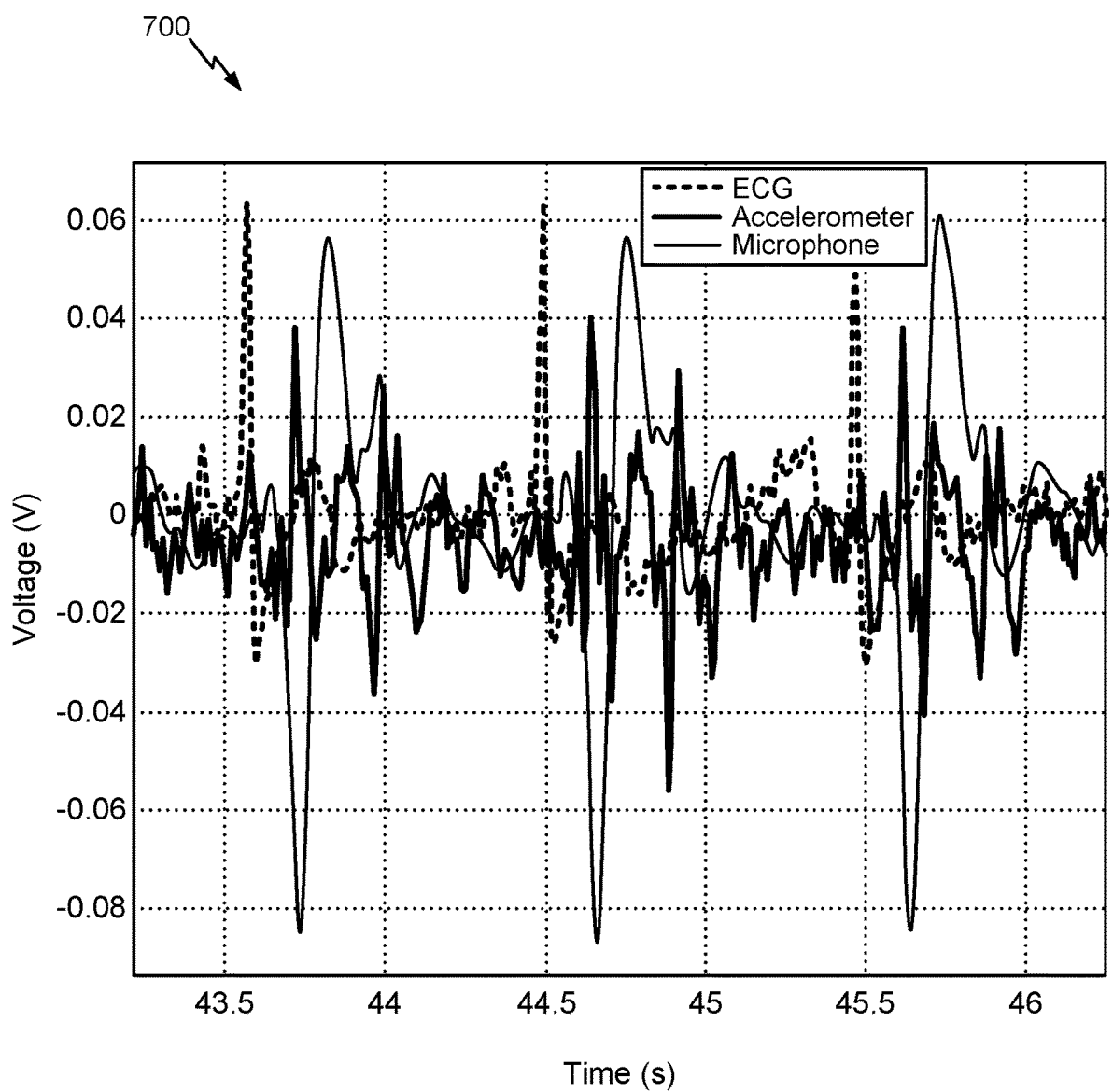
FIG. 7 illustrates an example of data used to obtain a PTT.

FIG. 7 illustrates an example of the data 700 used to obtain a PTT. The derived PTT may be used to determine a user's blood pressure. First, signal are obtained from different sensors, such as an ECG sensor, microphone, accelerometer, or optical, PPG sensor. The signal curves for an ECG signal, signal derived from an accelerometer, and signal derived from a microphone are illustrated in FIG. 7.

While not illustrated, the obtained signals are filtered, in an effort to enhance the signals. The signal can be filtered using frequency-based filtering, time averaging, and/or removing uncorrelated noise present in one signal but not the others. To remove uncorrelated noise, each sensor is used to enhance the signal obtained from other sensors.

After the signals are filtered, possibly relevant parameters from signal curves are extracted. One specific and important parameter is the PTT, which is the time delay between the different signals. The time delay can be computed in multiple ways such as peak-to-peak, trough-to-trough, or cross-correlations. According to aspects, the delay is calculated using a variety of methods and each of the derived quantities provides a different parameter. Other example parameters include the peak magnitudes, widths, and slope values.

Each of the collected parameters is correlated with diastolic or systolic blood pressure, for example, by computing Spearman's or Pearson's correlation coefficients. Correlated, relevant parameters are used to find the coefficients for a linear regression or polynomial regression, a logarithmic fit, or any machine learning technique that will predict blood pressure from the measurement of those parameters.

The pulse wave velocity is correlated to blood pressure. PTT is inversely proportional to pulse wave velocity, wherein the multiplicative factor is the distance between the two locations—a proximal location and a distal location. Therefore, PTT is correlated to blood pressure and can be used to predict blood pressure. More specifically, PTT is used to determine a change in a user's blood pressure. See, for example, Mukkamala, Ramakrishna, et al. "Toward Ubiquitous Blood Pressure Monitoring via Pulse Transit Time: Theory and Practice." *IEEE Transactions on Biomedical Engineering* 62.8 (2015): 1879-1901, for additional, publically-available information.

FIG. 7 illustrates an example plot of voltage versus time of the ECG signal, PCG signal, and accelerometer signal. Reference points are selected for each of the three signals to determine their time of occurrence. For example, a peak time or a trough time is selected for each of the ECG signal, the PCG signal, and the accelerometer signal.

According to an example, a delay between the signals is determined. For example, a peak of the ECG signal, a peak of the PCG signal, and a peak of the accelerometer signal are calculated. The delay is computed by cross-correlation, replica correlation, or various methods of signal averaging, such as using the ECG signal as a trigger to average the PCG signal. Relevant parameters are filtered and averaged over a few beats.

According to aspects, trough-to-trough delay, a maximum slope delay, a peak-to-peak delay, a peak value, a foot value, second peak value, or a pulse width are extracted from the ECG, PCG, and accelerometer signals in an effort to determine a user's blood pressure.

Multiple sensors are used to enhance the signals collected by each of the sensors. The multiple sensors are used to remove uncorrelated noise and the increase signal to noise ratio of collected signals. Use of the same sensors, such as an accelerometer, microphone, or optical sensor, on ear tips in both ears, will help improve the signal to noise ratio and remove uncorrelated noise.

Other biologically relevant information can be collected using the ear tip described herein. Heart rate, heart rate variability, and a respiratory rate can be determined using sensors on the ear tip. The heart rate is obtained by counting the number of peaks in a signal over a period of time, such as a minute, or by looking at the delay between two consecutive peaks of a same signal. The delay between two consecutive peaks may be referred to as an RR interval. Heart rate variability corresponds to statistics, such as a standard deviation, associated with the variations of the heart rate beat-to-beat. Accordingly, it is derived from delays between two consecutive peaks. A respiratory rate is derived from the beat-to-beat heart rate as a periodic oscillation of the heart rate over time. It is also derived from the beat-to-beat PTT as a periodic (almost sinusoidal) oscillation of this PTT over time.

Conductive Earpiece

Figure 8:
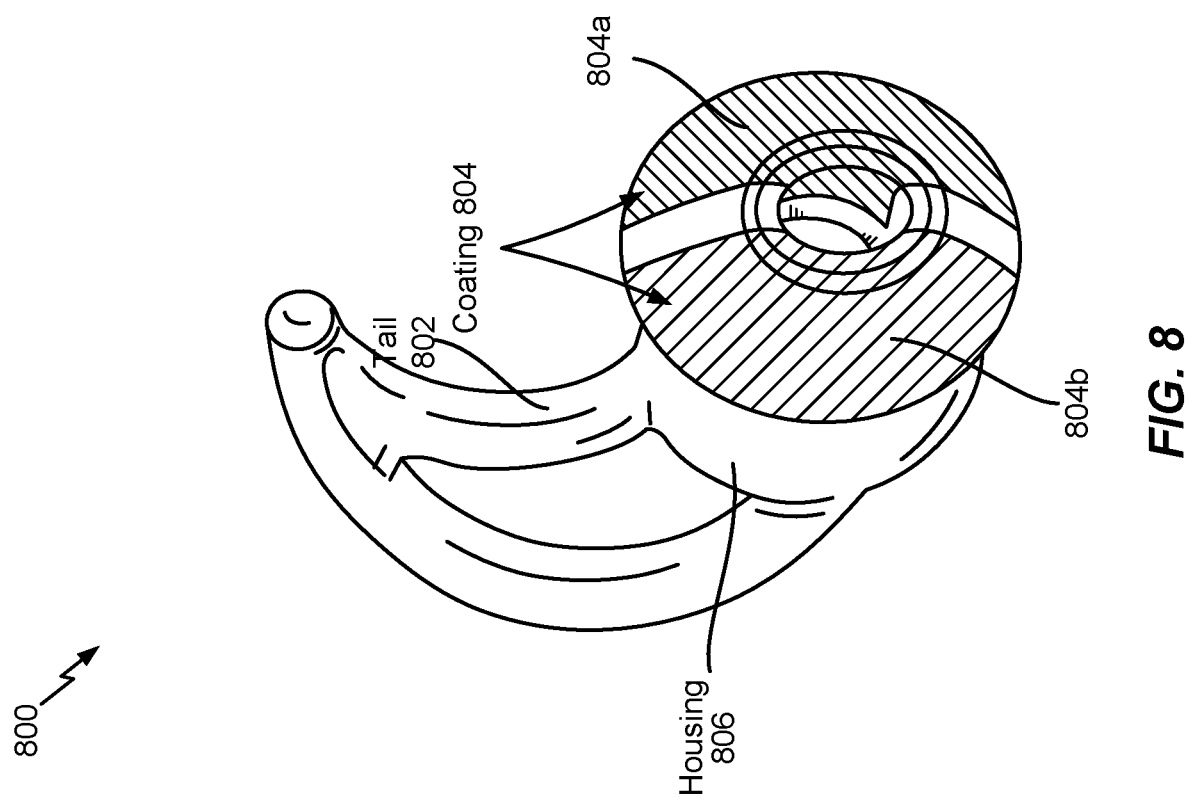
FIG. 8 illustrates an example earpiece including a coated, flexible, umbrella shaped ear tip and a tail portion.

FIG. 8 illustrates an example earpiece 800 including a coated, flexible, umbrella shaped ear tip and a tail portion. As illustrated in FIG. 8, the umbrella shaped ear tip is divided in two sections 804*a* and 804*b*. The tail is illustrated at 802. The housing 806 includes electronic hardware and a driver. According to one example, the housing is internal to the earpiece 800. For the earpiece to function as health monitoring system, the ear tip surface in contact with the skin of a user is conductive.

According to one example, the ear tip is coated with a conductive coating 804. The conductive coating can be continuous (not illustrated in FIG. 8) or can have more than one section. Each section 804*a*, 804*b* of the coating acts as a separate electrode used to collect biological information associated with a user. While two conductive coating sections are illustrated in FIG. 8, the earpiece 800 can have any integer number of conductive coatings. Having multiple electrodes is useful to compute GSR, EEG, EOG, EMG, or ECG as differences of potential. Additionally, having several sections wherein each section acts as a separate electrode improves the signal to noise ratio by removing uncorrelated noise.

According to an aspect, the conductive coating functions as an electrode to collect biological information associated with the user. The coating material may be one of Ag, AgCl/Ag, conductive carbon, graphene, or other biocompatible conductive material. The ear tip coated with one of these conductive coatings is used to collect information related to EEG, ECG, EOG, EMG, or GSR by contacting the skin of a user. In one example, the umbrella shaped ear tip of the earpiece contacts an interior portion of an ear canal. According to another example, the entire earpiece, including the umbrella shaped ear tip and tail, are coated with a conductive coating. The conductive coating can be continuous or can have more than one section.

Figure 9:
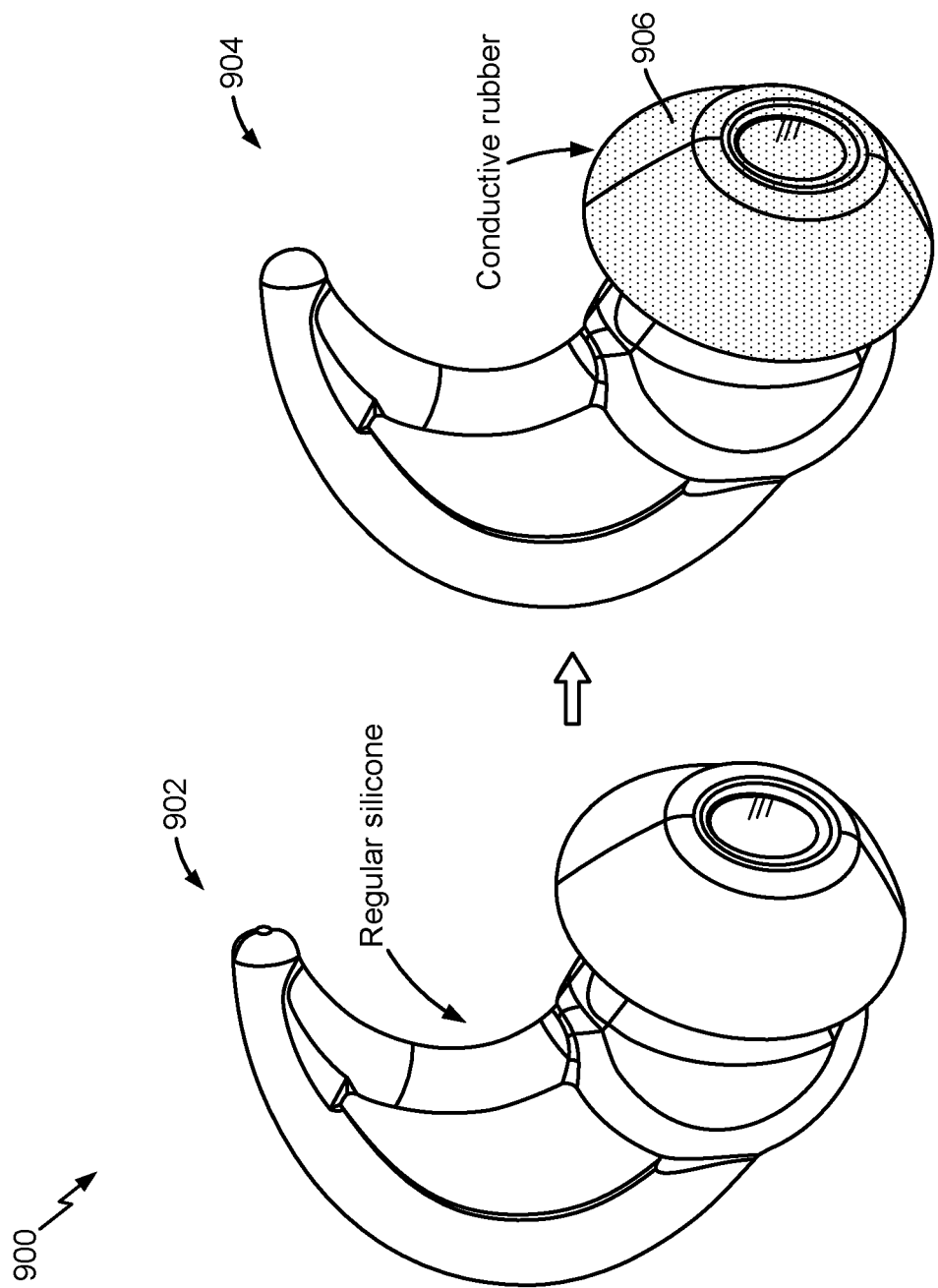
FIG. 9 illustrates example earpieces, each having a flexible, umbrella shaped ear tip.

FIG. 9 illustrates example earpieces 900, each having a flexible, umbrella shaped ear tip. As illustrated at 902, the entire earpiece is fabricated with silicone. As illustrated at 904, the umbrella-shaped ear tip 906 is fabricated with conductive rubber and the tail is fabricated with silicone. According to aspects, the conductive rubber used to fabricate the ear tip is made of a metal-filled substance such as silicone, polyurethane, or thermal plastic rubber. Using injection molding tools in the fabrication process of the ear tip 904, the conductive portions of the ear tip 906 can be electrically divided into several sections, wherein each section functions as an electrode. A conductive coating, as described with reference to FIG. 8, may be further added on top of the conductive rubber electrodes illustrated in FIG. 9.

Figure 10:
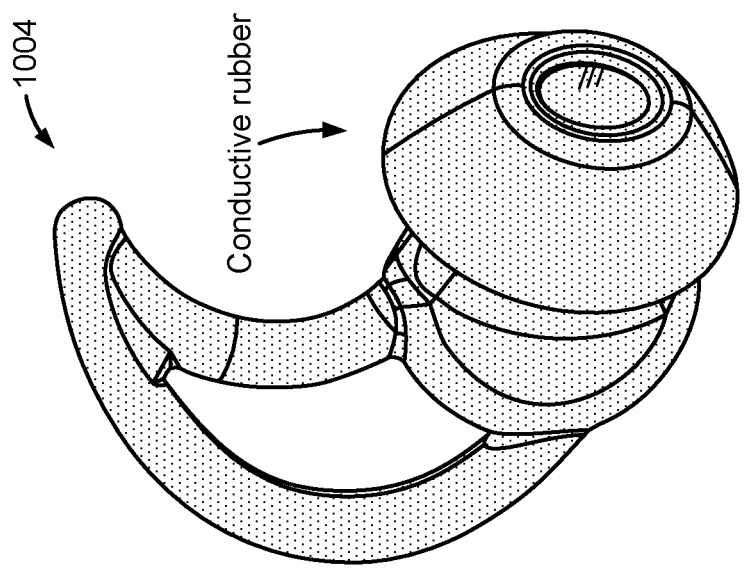
FIG. 10 illustrates example earpieces, each having a flexible, umbrella shaped ear tip.
Figure 10:
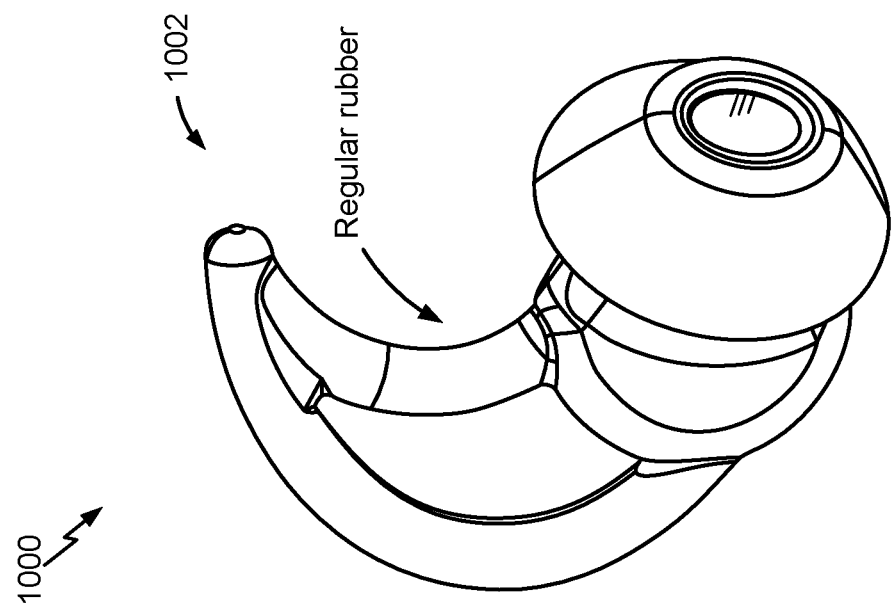

FIG. 10 illustrates example earpieces 1000 each having a flexible, umbrella shaped ear tip. As illustrated at 1002, the earpiece is fabricated with regular rubber. The earpiece 1004 is entirely covered with a conductive rubber. According to aspects, the conductive rubber used to fabricate the earpiece 1004 is texturized before coating. Using injection molding tools in the fabrication process of the earpiece 1004, the conductive portions of the earpiece can be electrically divided into several sections, wherein each section functions as an electrode.

As described above, the earpiece is made conductive by applying a coating (shown in FIG. 8) or by fabricating the earpiece or ear tip with a conductive material (shown in FIGS. 9 and 10). According to aspects, other biosensors are added to the earpiece. According to aspects, one or more optical sensors, microphones, or accelerometers are placed in the ear tip or in the housing internal to the earpiece. According to another example, biosensors monitor sweat composition, pH, etc. Sweat is produced and collected between skin and the ear tip. Accordingly, the ear tip is an advantageous location to collect enough sweat to determine properties of a user's sweat. Signals from the biosensors are transferred through the conductive coating for processing to extract biologically relevant information.

Figure 11:
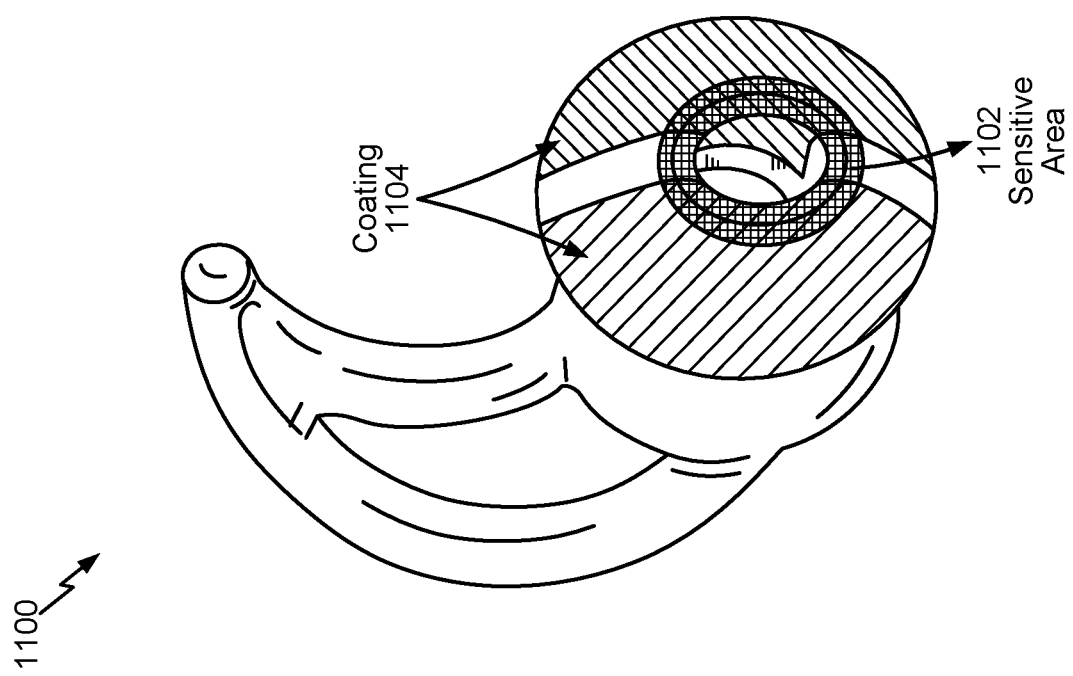
FIG. 11 illustrates an example earpiece with damage on the flexible ear tip.

FIG. 11 illustrates an example earpiece 1100 with damage on the flexible ear tip. For illustrative purposes, the ear tip is coated with a conductive coating 1104 as described with reference to FIG. 8; however, the earpiece or the ear tip 1100 could be fabricated with conductive rubber as shown in FIGS. 9 and 10. An electrode on the umbrella portion of the ear tip may crack or be damaged by handling. For example, a user applies pressure on the ear tip to place it in the ear canal. Specifically, the sensitive region 1102 of the ear tip gets damaged when the tip rubs the inner surface of the ear canal or becomes distorted during handling or insertion in the ear.

Figure 12:
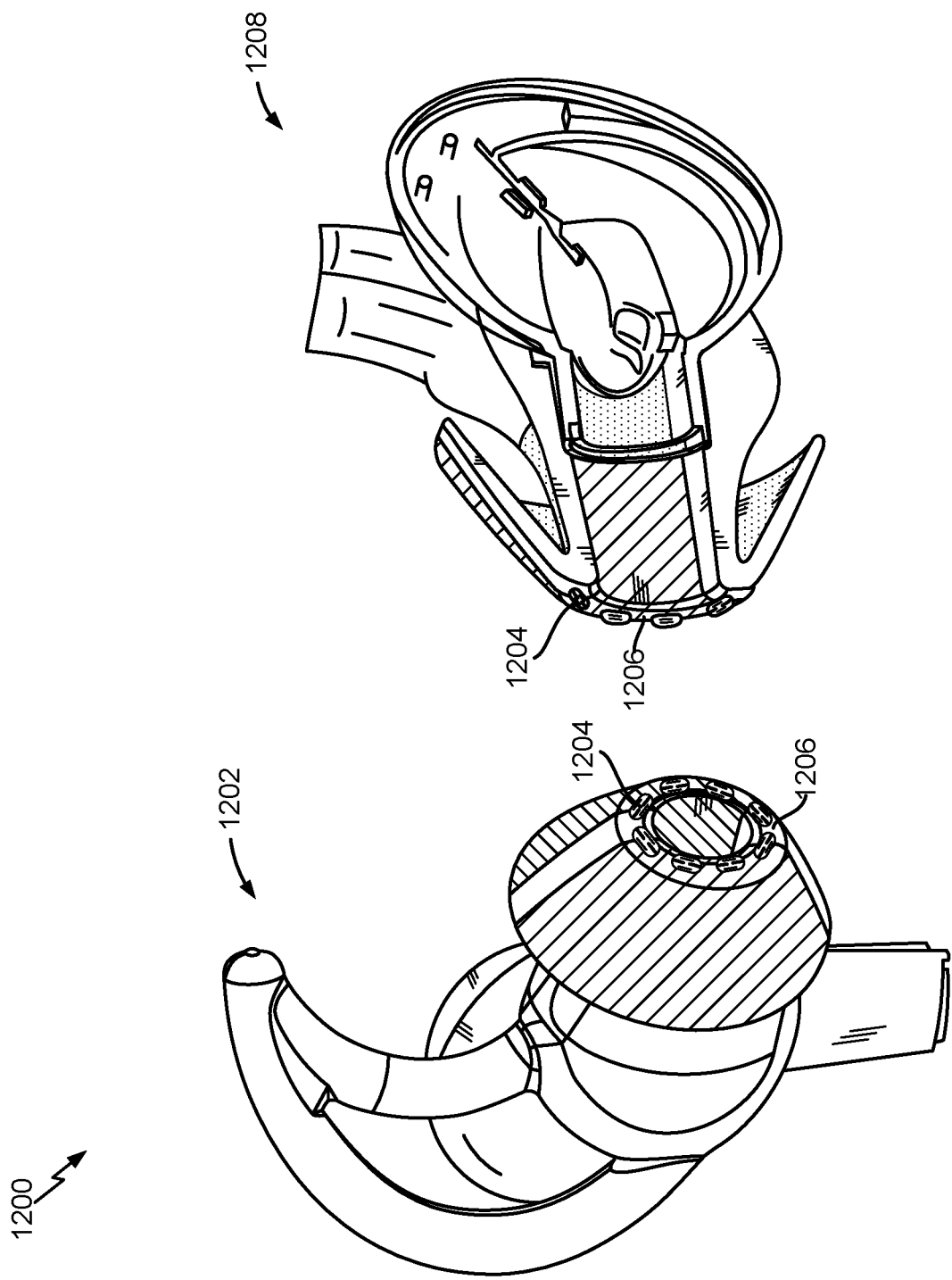
FIG. 12 illustrates an example earpiece including peaks and valleys on the umbrella shaped ear tip.

FIG. 12 illustrates an example earpiece 1200 including peaks and valleys on the umbrella shaped ear tip. Earpiece 1208 is a cross-sectional view of the earpiece 1202. The peaks 1204 and valleys 1206 on the umbrella shaped ear tip mitigate damage to the sensitive region of the ear tip. Only peaks 1204 will be rubbed off through handling of the ear tip. The valleys 1206 will provide electrical conductivity.

Figure 13:
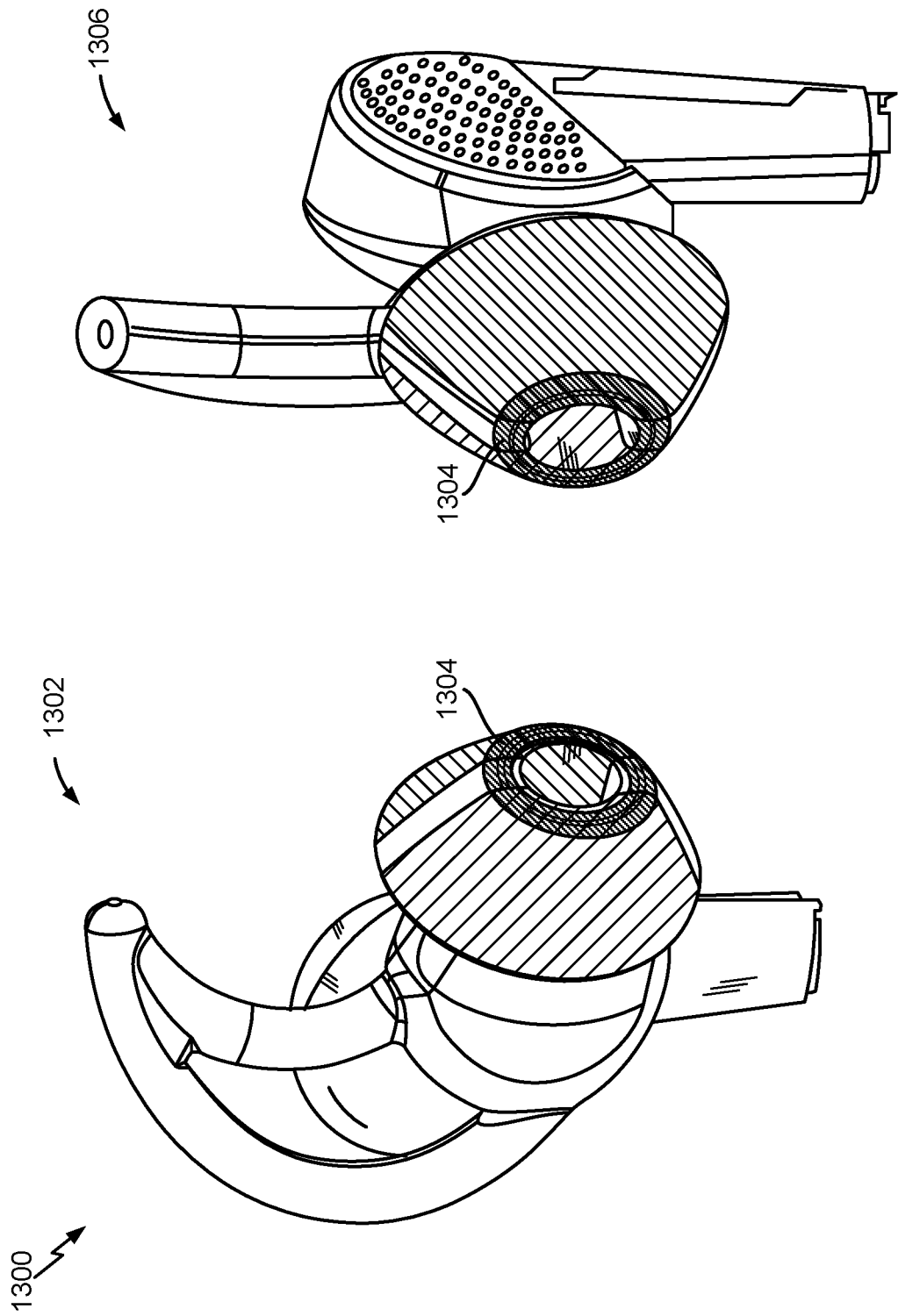
FIG. 13 illustrates an example earpiece having a protective coating on a portion of the umbrella shaped ear tip.

FIG. 13 illustrates an example earpiece 1300 having a protective coating on a portion of the umbrella shaped ear tip. 1302 and 1306 illustrate the same earpiece from different perspectives. A protective coating 1304 is applied on the sensitive region of the umbrella shaped ear tip to reduce damage to the ear tip and maintain conductivity.

Figure 14:
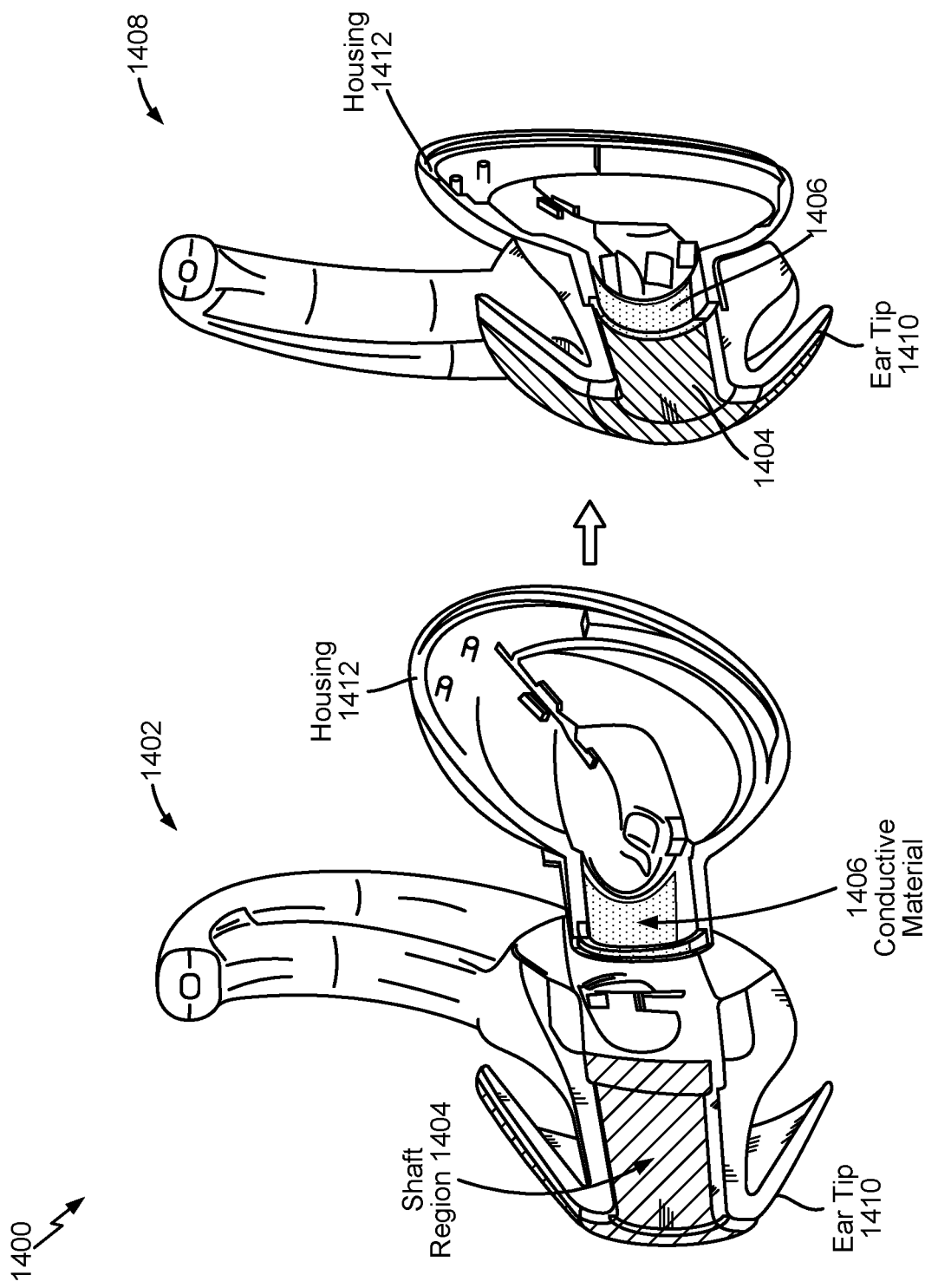
FIG. 14 illustrates an example cross-sectional representation of an earpiece.

FIG. 14 illustrates an example cross-sectional representation of an earpiece 1400, including an umbrella shaped ear tip, shaft region, and conductive material. 1402 and 1408 illustrate the same earpiece from different perspectives. The earpiece includes a shaft region 1404 between the ear tip 1410 and the housing 1412. An electrical signal moves from the exterior of the ear tip 1410 to the shaft region 1404. The signal is then transmitted to the plastic housing 1412 that holds electronics. To facilitate this transfer, the plastic housing has metal coextruded 1406 to provide a contact area to receive the signal from the coating in the shaft region 1404. This electrical connection method is also applicable if the ear tip is made from a conductive rubber as shown in FIG. 10. In another aspect, the plastic housing can remain insulating, and an electrical wire is attached to the shaft region 1404 and is connected to the electronics inside the plastic housing 1412.

As described above, a flexible, conductive ear tip contacts a surface of the ear of a user. The ear tip is configured to receive electrical signals from the user of the earpiece. The housing coupled with the ear tip is configured to transfer the electrical signals to electronic hardware for processing.

Figure 15:
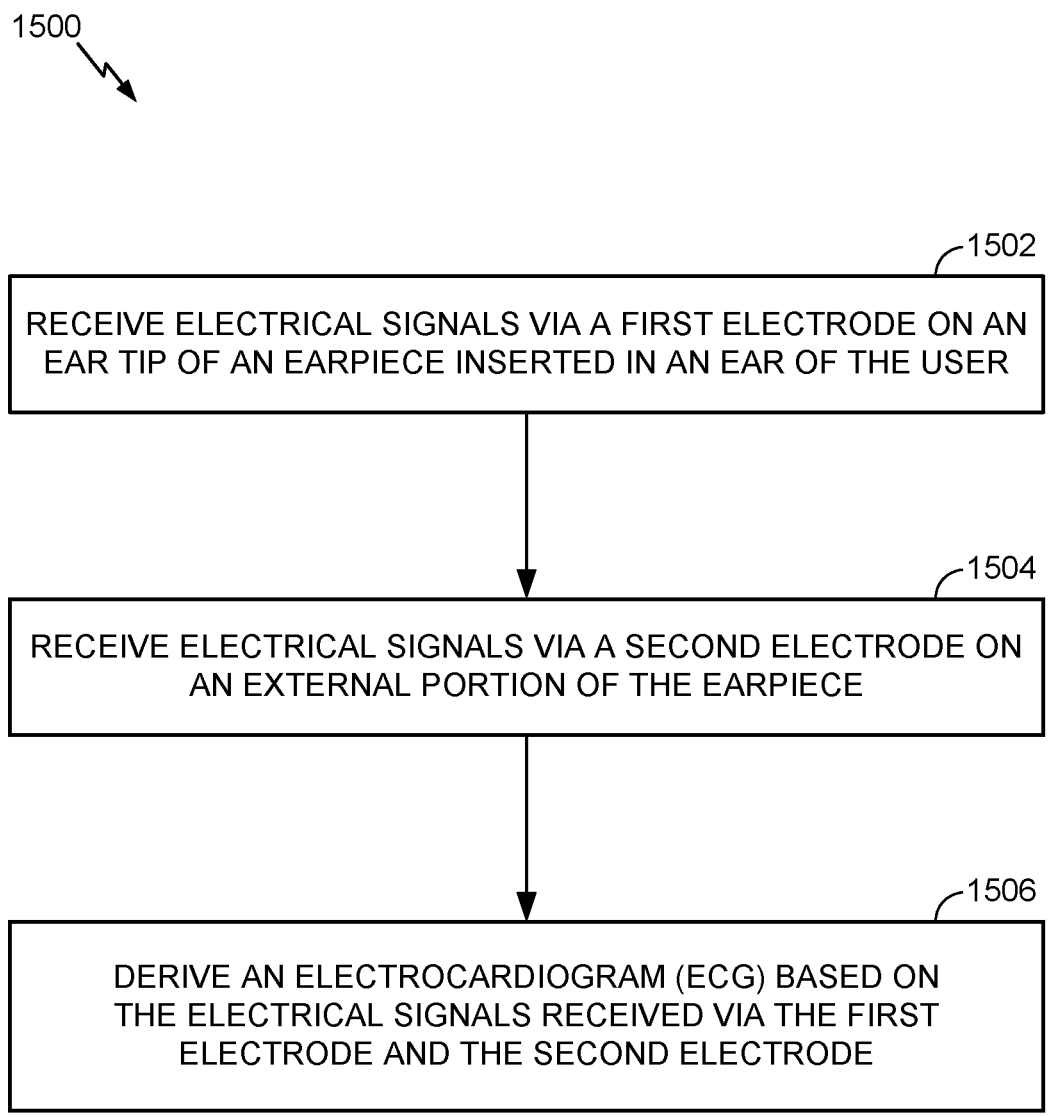
FIG. 15 illustrates example operations which may be performed to collect biologically-relevant information associated with a user.

FIG. 15 illustrates example operations 1500 which may be performed to collect biologically-relevant information associated with a user, in accordance with aspects of the present disclosure. At 1502, the electrical signals are received via a first electrode on an ear tip of an earpiece inserted in an ear of the user. At 1504, electrical signals are received via a second electrode on an external portion of the earpiece. At 1506, an ECG is derived based on the electrical signals received via the first electrode and the second electrode.

Figure 16:
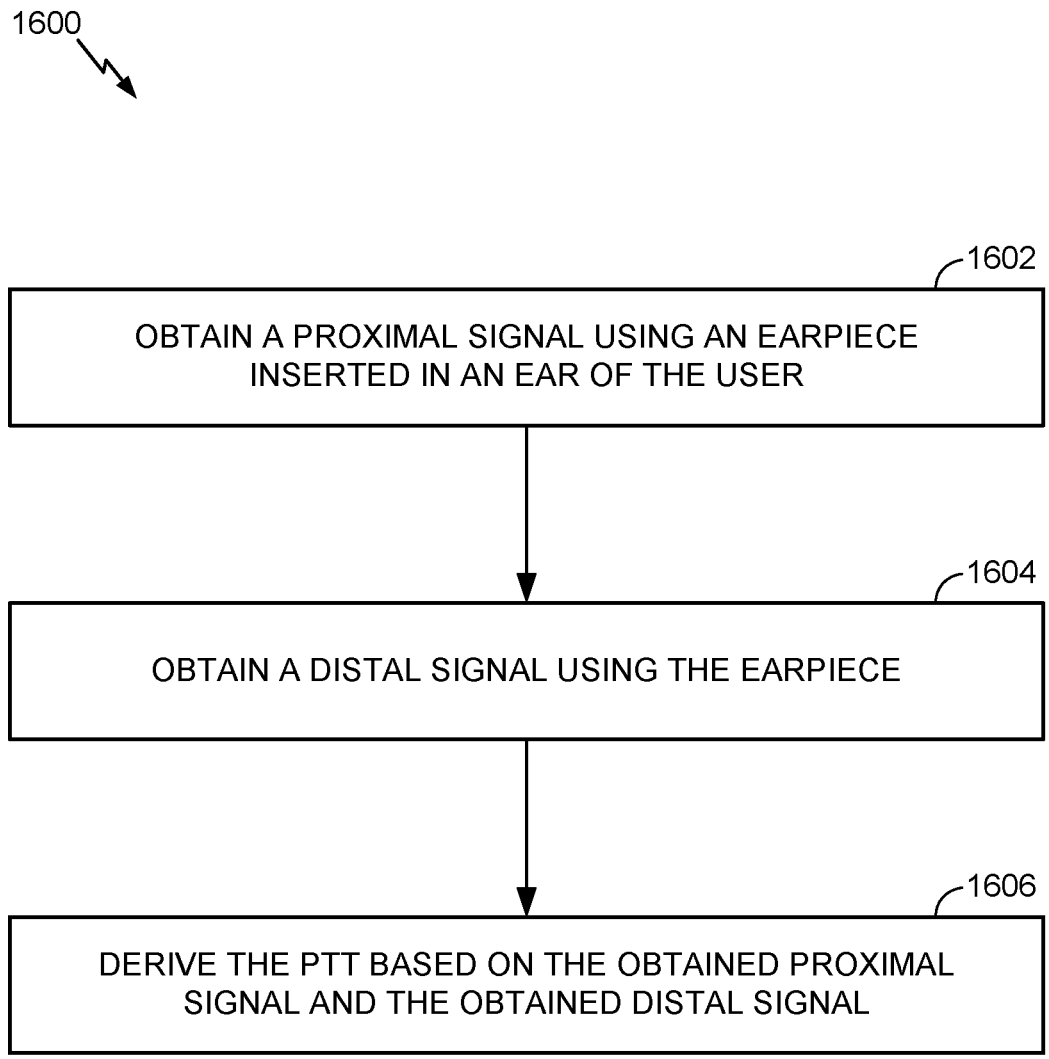
FIG. 16 illustrates example operations for determining a PTT associated with a user.

FIG. 16 illustrates example operations 1600 for determining a PTT associated with a user. At 1602, a proximal signal is obtained using an earpiece inserted in an ear of the user. At 1604, a distal signal is obtained using the earpiece. At 1606, the PTT is derived based on the obtained proximal signal and the obtained distal signal.

The operations 1500 and 1600 may be performed using an earpiece as described herein and illustrated in the figures. Accordingly, electrodes on an earpiece are used to measure an ECG at an ear. A PTT is derived using the earpiece.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. An earpiece comprising:
 a flexible, conductive ear tip coated with conductive coating or fabricated with conductive rubber, the conductive coating or conductive rubber configured to receive electrical signals from a user of the earpiece, wherein:
  the conductive coating or the conductive rubber is flexible,
  the conductive coating or conductive rubber of the conductive ear tip is continuous,
  the conductive ear tip comprises an umbrella shaped ear tip and is configured to create a seal with an ear canal of the user, and
  the conductive coating or the conductive rubber of the conductive ear tip comprises two or more sections, each section acting as a separate electrode for collecting electrical signals from the user;
 a housing coupled with the conductive ear tip, wherein the housing comprises electronics configured to transfer the electrical signals from the conductive ear tip to external electronic hardware; and
 an external electrode configured to be positioned external to the ear canal when the conductive ear tip is positioned in the ear canal, wherein the external electrode and the two or more sections form a sensor for collecting biologically relevant information associated with the user.

2. The earpiece of claim 1, further comprising:
 a biosensor placed on the earpiece, wherein the biosensor is configured to monitor at least one of sweat composition or pH associated with the user.

3. The earpiece of claim 2, wherein the conductive coating or conductive rubber of the conductive ear tip is configured to transfer signals from the biosensor to the housing.

4. The earpiece of claim 1, further comprising:
 multiple conductive electrodes for monitoring Galvanic Skin Response (GSR) of the user.

5. The earpiece of claim 1, wherein the electrical signals collected by the conductive ear tip are used to produce at least one of an electroencephalogram (EEG), electrocardiogram (ECG), electromyogram (EMG), or electrooculogram (EOG), associated with the user.

6. The earpiece of claim 1, further comprising:
a shaft region between the umbrella shaped tip and the housing; and
an electrical wire for transmitting the electrical signals from the shaft region to the housing, the electrical wire having a first end and a second end, wherein the first end is coupled with the shaft region and the second end is coupled with the housing.

7. The earpiece of claim 1, wherein the two or more sections are coated with a silver-based conductive coating and comprise a negative electrode and the external electrode comprises an isolated conductive coated section placed either on the conductive ear tip or the housing.

8. The earpiece of claim 1, wherein a portion of the housing is covered with copper foil to form the external electrode.

9. The earpiece of claim 1, further comprising:
at least one of a microphone, accelerometer, or optical sensor placed on the earpiece configured to collect biologically relevant information associated with the user.

10. The earpiece of claim 1, wherein the flexible, conductive ear tip is wholly flexible and conductive to the electrical signals.

11. The earpiece of claim 1, wherein the flexible, conductive ear tip is entirely coated with the conductive coating or entirely fabricated with the conductive rubber.

12. The earpiece of claim 1, wherein the housing is coupled to a surface of the conductive ear tip opposite the two or more sections.

* * * * *